United States Patent [19]

Tamaki et al.

[11] Patent Number: 5,344,777
[45] Date of Patent: Sep. 6, 1994

[54] STRUCTURAL GENE OF MEMBRANE-BOUND ALCOHOL DEHYDROGENASE COMPLEX, PLASMID CONTAINING THE SAME AND TRANSFORMED ACETIC ACID BACTERIA

[75] Inventors: Toshimi Tamaki, Handa; Hiroshi Takemura, Toda; Kenji Tayama, Handa; Masahiro Fukaya, Aichi; Hajime Okumura, Handa; Yoshiya Kawamura, Kounan, all of Japan

[73] Assignee: Nakano Vinegar Co., Ltd., Handa, Japan

[21] Appl. No.: 985,458

[22] Filed: Dec. 3, 1992

Related U.S. Application Data

[63] Continuation of Ser. No. 658,221, Feb. 20, 1991, abandoned.

[30] Foreign Application Priority Data

Feb. 26, 1990 [JP] Japan .................................. 2-42391
Mar. 26, 1990 [JP] Japan .................................. 2-73440

[51] Int. Cl.$^5$ ...................... C12N 15/53; C12N 15/31; C12N 15/74; C12N 1/21
[52] U.S. Cl. ............................... 435/252.3; 435/320.1; 435/69.1; 435/71.2; 435/172.3; 435/140; 435/190; 435/823; 530/401; 935/14; 935/24; 935/29; 935/66; 935/72
[58] Field of Search ................... 435/69.1, 71.2, 172.3, 435/190, 320.1, 823, 140; 530/401; 935/14, 24, 29, 66, 72

[56] References Cited

U.S. PATENT DOCUMENTS

4,394,443 7/1983 Weissman et al. ...................... 435/6
4,548,904 10/1985 Kent et al. ............................. 436/89

FOREIGN PATENT DOCUMENTS

60-9488 1/1985 Japan .
60-9489 1/1985 Japan .
63-12278 1/1988 Japan .
2-2364 1/1990 Japan .

OTHER PUBLICATIONS

Inoue et al., J. Bacteriology 171(6)3115–3112 (Jun. 1989).
Nunn et al., J. Bacteriology 166(2)581–590 (May 1986).
Entani et al., J. Gen. Appl. Microbiol., 31, 475–490 (1985), Japan.
Patent Abstracts of Japan, vol. 14, No. 126, Mar. 9, 1990, The Patent Office Japanese Government, Kokai No. 2-452, Japan.
Adachi et al., Agricultural and Biological Chemistry, 42, 2045–2056, 2331–2340 (1978).
Matushita et al., Agricultural and Biological Chemistry, 53, 2895–2902 (1989).
Methods in Enzymology, 73, 46–52 (1981).
Shu-Zen et al., Gene, 37, 267–269 (1985).
Ameyama et al., Agricultural and Biological Chemistry, 48, 561–565 (1984).
DNA Cloning, vol. 1, 109–135.
"Manual for Generic Engineering," 201–207 (1980).
Burnette, Analytical Biochemistry, 112, 195–203 (1991).
Okumura et al., Agricultural and Biological Chemistry, 49, 1011–1017 (1985).
Fukaya et al., Agricultural and Biological Chemistry, 49, 2091–2097, 2083–2090 (1985).
Adachi et al., Agricultural and Biological Chemistry, 44, 503–515 (1980).
Methods in Enzymology, vol. 101, "Recombinant DNA," 10, 20–28.
Inoue et al., Efficient Introduction of Vector Plasmids into Acetic Acid Bacteria, J. Ferment. Technol., vol. 63, No. 1, pp. 1–4, 1985.

Primary Examiner—Robert A. Wax
Assistant Examiner—Rebecca Prouty
Attorney, Agent, or Firm—Frishauf, Holtz, Goodman & Woodward

[57] ABSTRACT

There is provided a structural gene of membrane-bound alcohol dehydrogenase complex having a molecular size of about 7.0 kilo base which is derived from a microorganism belonging to the genus Acetobacter represented by *Acetobacter altoacetigenes* and shown by the nucleotide sequence of SEQ ID. NO. 1 and SEQ ID NO. 2. This enzyme increases the efficiency of acetic acid fermentation and may be effectively utilized for quantitative determination of alcohol.

2 Claims, 1 Drawing Sheet

STRUCTURAL GENE OF MEMBRANE-BOUND ALCOHOL DEHYDROGENASE COMPLEX, PLASMID CONTAINING THE SAME AND TRANSFORMED ACETIC ACID BACTERIA

This application is a continuation, of application Ser. No. 07/658,221, filed Feb. 20. 1991, now abandoned.

BACKGROUND OF THE INVENTION

1. Field of the Invention

The present invention relates to a structural gene of membrane-bound alcohol dehydrogenase complex derived from a microorganism belonging to the genus Acetobacter, and a plasmid containing the same as well as its utilization.

2. Brief Description of Related Art

A membrane-bound alcohol dehydrogenase produced by a microorganism belonging to the genus Acetobacter is an enzyme which oxidizes an alcohol into the corresponding alcohol. The enzyme takes a part in oxidative fermentation of acetic acid fermentation for producing acetic acid from ethanol, and is also utilized for quantitative determination of alcohol; the enzyme is useful from an industrial viewpoint.

Heretofore the membrane-bound alcohol dehydrogenase (hereafter simply referred to as ADH) has been obtained by culturing a microorganism belonging to the genus Acetobacter or the genus Gluconobacter, extracting and purifying from the cultured cells and has been utilized (Agricultural and Biological Chemistry, 42, 2045, 1978; ibid., 42, 2331, 1978).

For purification of this enzyme, however, fractionation by complicated column chromatography was required so that it was difficult to prepare the enzyme in large quantities. In addition, the enzyme is unstable and cannot be stored over a long period of time, which has been a problem in its application.

In order to solve these problems, it is considered to harvest mutants having an enhanced enzyme content in the cells by a mutation treatment. However, there is no report yet that any mutant having a sufficient enzyme content was harvested. It is also considered to achieve the object by cloning a gene of the enzyme and increasing the copy number of the enzyme gene or enhancing an expression degree, through genetic engineering technology. For this attempt, ADH gene of *Acetobacter aceti* K6033 strain has been cloned and its nucleotide sequence has been determined (Journal of Bacteriology, 171, 3115, 1989). This study is expected to be effective for improving the productivity of the enzyme by genetic engineering technology. In actuality, however, even though a plasmid carrying the enzyme gene is introduced into a host of acetic acid bacteria, the enzyme activity is not improved more than the activity inherently possessed by the host and such technique is not practical.

This is believed to be because the cloned gene would be composed only of subunits having a larger molecular weight out of the subunits constructing ADH. Any conventional ADH is purified in the form of a complex with cytochrome c from acetic acid bacteria. Matsushita et al. reported that the activity of ADH was affected depending upon the quantity of cytochrome c and cytochrome c was not present merely as an impurity but took a part in expressing the enzyme activity (Agricultural and Biological Chemistry, 53, 2895, 1989). For this reason, it was necessary to increase the subunits having a large molecular weight and at the same time, increase the amount of the subunits of cytochrome c.

Furthermore, properties of the enzyme in the cloned *Acetobacter aceti* K6033 strain were not studied and utility of the enzyme of K6033 strain is unclear.

In order to solve the foregoing problems, the present inventors have brought attention to ADH produced by a series of microorganisms belonging to the genus Acetobacter represented by *Acetobacter altoacetigenes*, which are already known to have enzymatically excellent properties, and have succeeded in cloning the structural gene of two proteins (subunits) constructing ADH and in carrying the structural gene on a plasmid.

Furthermore, the present inventors have found that by using the plasmid carrying the cloned gene, the content of this enzyme in the cells can be increased, ADH can be readily extracted and purified and, an efficiency of acetic acid fermentation can be improved. The present invention has thus been accomplished.

SUMMARY OF THE INVENTION

That is, the present invention relates to a structural gene of ADH complex which is derived from a microorganism belonging to the genus Acetobacter, is shown by restriction enzyme map of FIG. 1 and has a molecular size of about 7.0 kilobase, and a plasmid carrying the gene as well as a microorganism belonging to the genus Acetobacter or the genus Gluconobacter transformed with the plasmid. The present invention further relates to a structural gene of a protein constituting an ADH complex, which is represented by nucleotide sequence shown in SEQ ID NO: 1 and has a molecular weight of about 72,000, and a plasmid carrying the gene as well as a microorganism belonging to the genus Acetobacter or the genus Gluconobacter transformed with the plasmid. The present invention also relates to a structural gene of a protein constituting an ADH complex, which is represented by nucleotide sequence shown in SEQ ID NO: 2 and has a molecular weight of about 44,000, and a plasmid carrying the gene as well as a microorganism belonging to the genus Acetobacter or the genus Gluconobacter transformed with the plasmid.

BRIEF DESCRIPTION OF THE SEQUENCES

Figure 1:
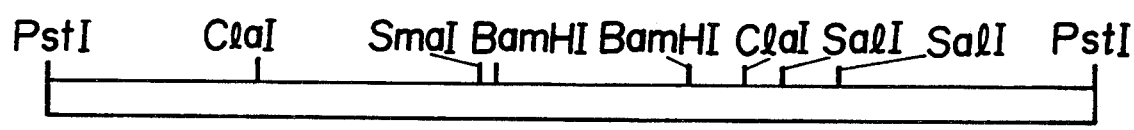
FIG. 1 shows restriction enzyme map of the structural gene of a membrane-bound alcohol dehydrogenase complex isolated using Pst I.

SEQ ID NO. 1 shows the nucleotide sequence of the structural gene of a protein having a molecular weight of about 72,000 which constitutes a membrane-bound alcohol dehydrogenase complex isolated using Sma I, and SEQ ID NO. 3 shows amino acid sequence determined from the nucleotide sequence of the structural gene of a membrane-bound alcohol dehydrogenase complex.

SEQ ID NO. 2 shows the nucleotide sequence of the structural gene of a protein having a molecular weight of about 44,000 which constitutes a membrane-bound alcohol dehydrogenase complex isolated using Pst I, and SEQ ID NO. 4 shows amino acid sequence determined from the nucleotide sequence of the structural gene of a membrane-bound alcohol dehydrogenase complex. Abbreviations in the amino acid sequences are used to mean the following:

| Met | methionine | Ala | alanine |
|---|---|---|---|
| Arg | arginine | Asn | asparagine |
| Asp | aspartic acid | Cys | cystein |
| Gln | glutamine | Glu | glutamic acid |
| Gly | glycine | His | histidine |
| Ile | isoleucine | Leu | leucine |
| Lys | lysine | Phe | phenylalanine |
| Pro | proline | Ser | serine |
| Thr | threonine | Trp | tryptophan |
| Tyr | tyrosine | Val | valine |

DETAILED DESCRIPTION OF THE PREFERRED EMBODIMENTS

The membrane-bound alcohol dehydrogenase complex in the present invention refers to a novel alcohol dehydrogenase complex having excellent stability which is described in Japanese Patent Application Laid-Open No. 63-12278 and composed of two proteins having molecular weights of about 72,000 and about 44,000. This enzyme is produced by a series of microorganisms belonging to the genus Acetobacter represented by *Acetobacter altoacetigenes* MH-24 (FERM BP-491).

The gene fragment containing the structural gene of the enzyme can be cloned from the total DNA which the microorganism belonging to the genus Acetobacter capable of producing this enzyme carries. The total DNA may be prepared by, for example, the method disclosed in Japanese Patent Application Laid-Open No. 60-9489. The gene fragment containing the structural gene of the ADH complex may be cloned from the total DNA by, for example, procedures shown in Example 1, that is, determining a part of the amino acid sequence of this enzyme, preparing synthetic DNA corresponding to the determined amino acid sequence and selecting a clone having the desired gene utilizing the synthetic DNA as a probe; etc. The amino acid sequence may be determined as follows: after the alcohol dehydrogenase complex purified by the method disclosed in Japanese Patent Application Laid-Open No. 63-12278 is separated into two subunits by SDS-polyacrylamide gel electrophoresis, the protein corresponding to each subunit is extracted from the gel in a conventional manner such as electric dialysis, etc. The extracted protein is used for determination of amino acid sequence at the amino terminus as it is. Alternatively, after the protein is cleaved with CNBr or with a protease (peptidase) having a high specificity, the cleavage product is fractionated by gel filtration, etc. and the resulting fraction is used for determination of amino acid sequence at the amino terminus in a conventional manner using an amino acid sequencer, etc. Synthesis of DNA corresponding to the thus determined amino acid sequence may be carried out in a conventional manner.

An antibody to the enzyme may be prepared by separating into two subunits the alcohol dehydrogenase complex purified by the method disclosed in Japanese Patent Application Laid-Open No. 63-12278 by SDS-polyacrylamide gel electrophoresis, extracting the protein corresponding to each subunit from the gel in a conventional manner such as electric dialysis, etc. and using the extracted protein as an antigen. Specifically, anti-ADH antibody may be obtained by, for example, the method described in "Methods in Enzymology", 73, 46 (1981). About 2 weeks after the first immunization, second immunization is made and in a month to a month and a half, the production of the antibody specific to ADH is observed. This antibody may be further purified either through purification by ammonium sulfate fractionation, etc. or by ion exchange chromatography. In the case that the antibody is used to clone the gene, it may also be possible to use appropriately diluted serum.

On the other hand, the cleavage product of the total DNA with an appropriate restriction enzyme is ligated with the cleavage product of an appropriate vector with a restriction enzyme capable of ligating with the total DNA using T4 DNA ligase. The ligation product is transformed to *E. coli* host. Examples of the vector used in this case include vectors of *E. coli* generally used, such as pBR322, pUC18, pUC19, and the like.

Transformation of *E. coli* may be conducted in a conventional manner. Detection of a strain bearing the desired gene can be made by preparing synthetic DNA based on the amino acid sequence previously determined using the purified enzyme and performing conventional colony hybridization using the synthetic DNA as a probe, whereby a strain reactive with the probe is selected.

Also where antigen-antibody reaction is utilized, a strain carrying the desired gene may be detected by a method similar to, e.g., Gene, 37, 267 (1985). That is, the lysate of the resulting transformants is reacted with the antibody and a strain showing a specific reaction may be selected.

The strain selected by the procedures described above may have a plasmid carrying the gene fragment having the entire length of the desired gene but may sometimes carry merely a part of the gene.

Where the strain has merely a part of the gene, the entire length of the gene may be obtained by using as a probe the gene already obtained and isolating a fraction showing homology to the probe by Southern hybridization, etc.

The nucleotide sequence of the resulting gene may be determined in a conventional manner, for example, by the dideoxy method using M13 phage.

In order to produce the ADH complex or the proteins constructing the ADH complex using the thus isolated gene fragment containing the structural gene of the ADH complex, in general, it is necessary to ligate the gene fragment carrying the enzyme gene with a gene having a promoter activity functioning in a host in the form of capable of expression. As the promoter used to produce the ADH complex proteins in a microorganism belonging to the genus Acetobacter or the genus Gluconobacter, there may be used a promoter inherently possessed by the ADH complex gene and there may also be used an acetic acid bacteria-derived gene having other promoter activity and a promoter of *E. coli* capable of expressing in acetic acid bacteria. As the *E. coli* promoter, there may be used promoters of ampicillin-resistant gene of *E. coli* plasmid pBR322, kanamycin-resistant gene of *E. coli* plasmid pACYC177, chloram-phenicol-resistant gene of *E. coli* plasmid pACYC184, β-galactosidase gene of *E. coli*, etc. Where the ADH complex is produced in an excess amount to affect growth or the like of the host, it is necessary to choose an appropriate promoter for controlling an expression amount of the gene. Where the gene is expressed, formation of a protein having a size different from the molecular weight of the gene is sometimes observed. This is because the protein is produced in a host in the form of a fused protein in which other protein is fused. However, if the fused protein is produced in such a form that its enzyme activity can be expressed, there would be no problem.

As the vector for carrying the gene fragment containing the structural gene of the ADH complex in acetic acid bacteria, there may be utilized, for example, pTA5001(A) and pTA5001(B) disclosed in Japanese Patent Application Laid-Open No. 60-9488; wide host range vectors RP4::Mu, RP4, pRK2013, RSF1010, etc. which can be introduced into acetic acid bacteria.

For expression of the activity of ADH, it is necessary that the two proteins constituting the ADH complex be produced efficiently with good balance, as shown in the EXAMPLES. In general, the gene fragment containing the structural gene of the ADH complex is used as it is and the two proteins may be expressed on the same level. Depending upon acetic acid bacteria, however, either protein is not sufficiently possessed in some occasion. In this case, it is required that the gene encoding the two proteins are independently prepared and the genes having a promoter activity used to express the genes are selected to be a suitable expression amount, respectively. For controlling the expression amount, it may also be possible to use different vectors in the two genes and utilize a difference in the copy number of the vectors in acetic acid bacteria.

As stated above, the plasmid containing the structural gene of the ADH complex can be isolated. After transformation, the gene is expressed, whereby the protein constituting the ADH complex can be produced in a marked quantity.

As the host for producing the ADH complex, microorganisms such as E. coli, Bacillus subtilis, etc. on which genetic engineering technique has been established may be used. However, it is more advantageous to use acetic acid bacteria which inherently possess the ability of producing the ADH complex, namely, the microorganisms belonging to the genus Acetobacter or the genus Gluconobacter.

ADH has pyrroloquinoline quinone (PQQ) as its prosthetic group. In order to produce an activated enzyme, PQQ may be supplemented to a medium, etc. to produce the ADH complex protein. However, as is described in Agricultural & Biological Chemistry, 48, 561 (1984), the ability of E. coli or S. subtilis for synthesizing PQQ is poor and it has been revealed that the synthesizing ability of acetic acid bacteria is high. It is thus advantageous for the host to have the ability for synthesizing PQQ.

Further in acetic acid fermentation, ADH participates in the reaction of oxidizing ethanol to acetaldehyde. For this reason, by enhancing the content of the ADH complex in acetic acid bacteria, it can be expected to make the acetic acid fermentation efficient. In this case, where ADH alone is expressed excessively, the concentration of acetaldehyde, which is the oxidation product of ethanol, increases so that acetic acid bacteria are damaged by strongly cytotoxic acetaldehyde. Therefore, it is necessary either to control the amount of the ADH complex gene expressed to the amount corresponding to the oxidizing activity of acetaldehyde or to increase the amount of aldehyde dehydrogenase at the same time, using the structural gene of the membrane-bound aldehyde dehydrogenase recited in Japanese Patent Application Laid-Open No. 2-2364 so as not to cause excessive accumulation of acetaldehyde.

EXAMPLES

Next, the present invention is described in detail by referring to the examples below.

Example 1

Determination of amino terminal amino acid sequence and preparation of synthetic probe Acetobacter altoacetigenes MH-24 (FERM BP-491) strain was shaking cultured at 30° C. in medium composed with 3% of glucose, 4% (V/V) of ethanol, 6% (V/V) of acetic acid, 0.5% of yeast extract (manufactured by Daigo Nutrient Chemistry Co., Ltd.) and 0.2% of polypeptone (manufactued by Daigo Nutrient Chemistry Co., Ltd.).

After the incubation, the cells were harvested by centrifugation and 10 mg of the ADH complex was then obtained in a conventional manner (the method disclosed in Japanese Patent Application Laid-Open No. 63-12278). This complex was subjected to SDS-polyacrylamide gel electrophoresis to separate the protein having a molecular weight of about 72,000 and the protein having a molecular weight of about 44,000. Then, the protein of 72,000 was eluted from the gel in a conventional manner and provided as a sample for the following experiment.

After 1 mg of the sample obtained was cleaved with lysyl endopeptidase (manufactured by Wako Pure Chemicals, Inc.), the cleavage product was fractionated by HPLC LC-4A manufactured by Shimadzu Seisakusho Co., Ltd. As a column Senshu Pak. VP-304-1251 (4.6$\phi$×250 mm) was used and the elution was performed at a flow rate of 1 ml/min and at room temperature by linear gradient of acetonitrile-water (containing 0.1% trifluoroacetic acid) of 0 to 55%. By monitoring at absorbance of 220 nm, 11 peaks were noted. From the earlier order of elution, the second, ninth and eleventh peaks were fractionated. About 0.5 mg of the fractionated product was applied to amino acid sequencer Model 470A manufactured by Applied Biosystems Inc. to determine the amino terminal amino acid sequence. The results reveal that the sequence of the peptide eluted in the ninth order was: Thr-Gly-Leu-Val-Tyr-Ile-Pro-Ala-Gln-Gln-Val-Pro-Phe-Leu-Tyr-Thr-Asn-Gln-Val-Gly-Gly-Phe-Tyr-Pro-His-Pro-Asp; and that the sequence of the peptide eluted in the ninth order was: Leu-Ala-Trp-Tyr-Leu-Asp-Leu-Asp-Thr-Asn-Arg-Gly-Gln-Glu-Gly-Thr-Pro-Leu. Furthermore, the sequence of the peptide eluted in the second order was: Asn-Tyr-Val-Tyr-Val-Asn-Trp-Ala-Ser-Gly-Leu-Asp-Pro.

The protein having a molecular weight of 72,000 which was not treated with lysyl endopeptidase was analyzed by the amino acid sequencer. The amino terminal amino acid sequence was Asp-Asp-Gly-Gln-Gly. DNA corresponding to the amino acid sequence was synthesized with DNA synthesizer 381A manufactured by Applied Biosystems Inc., based on the two sequences of Tyr-Ile-Pro-Ala-Gln-Gln-Val (Sequence 1) and Val-Ile-Ile-Gly-Asn-Gly (Sequence 2) in the amino acid sequence of the peptide eluted in the ninth order and a part of the amino acid sequence, Try-Val-Tyr-Val-Asn-Trp-Ala (sequence 3), in the peptide eluted in the second order, taking utilization of codon into account.

For Sequence 1, Probe 1 of 20-mer, composed of 64 kinds, shown by:

```
      T  T
   TA  AT  CCNGCNCAGCAGCAGG
      C  C
``` and for Sequence 2, Probe 2 of 17-mer, composed of 128 kinds, shown by:

```
         T  T       T
   GTNAT  AT  GGNAA  GG
         C  C       C
``` were synthesized, respectively. For Sequence 3, Probe 3 of 20-mer, composed of 128 kinds, shown by:

```
        A       A    A A
   GCCCA  TTNAC  TAN C TA
        G       G   G G
``` which was a sequence of the complementary chain, was synthesized.

Cloning of the structural gene of protein having a molecular weight of about 72,000 which constructs the ADH complex From the cells of *Acetobacter altoacetigenes* MH-24 strain which had been obtained by culturing as described above, the total DNA was prepared in a conventional manner (the method disclosed in Japanese Patent Application Laid-Open No. 60-9489). After the total DNA was cleaved with restriction enzyme, Pst I or Sma I (manufactured by Takara Shuzo Co., Ltd.), the product was ligated with *E. coli* vector pUC18 (manufactured by Takara Shuzo Co., Ltd.) which was cleaved with Pst I or Sma I, thereafter dephosphorylated with bacterial alkaline phosphatase (manufactured by Takara Shuzo Co., Ltd.), using T4 DNA ligase (manufactured by Takara Shuzo Co., Ltd.). After the ligation mixture was transformed to *E. coli* JM 109 host by the method of Hanahan ["DNA Cloning", 1, 109, IRL Press (1985)], the transformants were selected in LB agar medium ("A Manual for Genetic Engineering", page 201, Cold Spring Harbor Laboratory, 1980) containing ampicillin in a concentration of 30 μg/ml.

With respect to about 5,000 recombinants obtained, colonies which hybridized with Probe 2 and Probe 3 described above were detected according to the colony hybridization technique (Molecular Cloning, A Laboratory Manual, T. Maniatis et al, page 312, Cold Spring Harbor Laboratory, 1980) using the two probes. In Pst I, three (3) clones were hybridized with Probes 2 and 3 and in Sma I, two (2) clones were hybridized with the probes. Furthermore, these 5 clones all were hybridized also with Probe 1.

Figure 2:
FIG. 2 shows restriction enzyme map of the structural gene of a protein having a molecular weight of about 72,000 which constitutes a membrane-bound alcohol dehydrogenase complex isolated using Sma I.

Analysis with restriction enzyme reveals that all of the 3 clones obtained using Pst I had the same fragment of about 7.0 kilo base at the Pst I site of pUC18. Further in the case of Sma I, the clones had the same fragment of about 4.5 kilo base. The fragment of about 7.0 kilo base obtained with Pst I had a portion of about 4.1 kilo base in common to the fragment of about 4.5 kilo base. The plasmid (chimera plasmid composed of pUC18 and the insert fragment of about 7.0 kilo base, named pADHP1) possessed by 1 clone obtained using Pst I was transformed in *E. coli* JM 109 and has been deposited in the Fermentation Research Institute of the Agency of Industrial Science and Technology of Japan under the name of *E. coli* ADHP-1 as [FERM BP-3254 (FERM P-11278)]. The restriction enzyme map of the insert fragment of about 7.0 kilo base was prepared in a conventional manner, which is as shown in FIG. 1. Furthermore, the plasmid (chimera plasmid composed of pUC18 and the insert fragment of about 4.5 kilo base, named pADHS1) possessed by 1 clone obtained using Sma I was transformed in *E. coli* JM 109 and has been deposited in the Fermentation Research Institute of the Agency of Industrial Science and Technology of Japan under the name of *E. coli* ADHS-1 as [FERM BP-3253 (FERM P-11201)]. The restriction enzyme map of the insert fragment of about 4.5 kilo base was prepared in a conventional manner, which is as shown in FIG. 2.

With respect to the insert fragment of pADHS1, its nucleotide sequence was determined by the dideoxy method [Methods in Enzymology, 10, 20, Academic Press, New York, 1983) using M13 phage.

Based on the thus determined nucleotide sequence, an open-reading frame was surveyed. The open-reading frame encoding 738 amino acid residues (molecular weight of 80839) and composing of 2214 bases translated from ATG initiation codon as shown in SEQ ID NO. 3 was noted in the portion common to the Sma I fragment having a size of about 4.5 kilo base and the Pst I fragment having a size of about 7.0 kilo base (the amino acid sequence determined from the nucleotide sequence of SEQ ID NO. 1 is shown in SEQ ID NO. 2. The polypeptide shown by the nucleotide sequence of SEQ ID NO. 1 coincides with the protein having a molecular weight of about 72,000 which constitutes the membrane-bound alcohol dehydrogenase complex of the present invention. This is confirmed by the fact that when the amino acid sequence of the purified protein having a molecular weight of about 72,000, which constructs the membrane-bound alcohol dehydrogenase complex of the present invention, was determined by the method described above, the sequence fully coincident with the amino terminal amino acid sequences of the 3 peptides of the lysyl endopeptidase cleavage products was found. That is, the sequence of 27 amino acids of the peptide eluted in the ninth order coincided with the sequence of 27 amino acids following 442 amino acid from the amino terminus deduced from the nucleotide sequence. Furthermore, the sequence of 18 amino acids of the peptide eluted in the eleventh order coincided with the sequence of 18 amino acids following 84 amino acid deduced from the nucleotide sequence. The amino terminal amino acid sequence of the peptide eluted in the second order coincided with the sequence of 13 amino acids following 389 amino acid deduced from the nucleotide sequence.

Furthermore, the amino terminal sequence (Asp-Asp-Gly-Gln-Gly) of the purified protein completely coincided with the amino acid sequence following the 36th counted from the amino terminus which is deduced from the nucleotide sequence. It is thus assumed that the amino acid sequence up to the 35th from the amino terminus deduced from the nucleotide sequence would be the region which participates in secretion of the protein having a molecular weight of about 72,000. *Acetobacter aceti* K6033 strain had homology of about 77% to ADH gene in the amino acid sequence.

Preparation of anti-ADH antibody

*Acetobacter altoacetigenes* MH-24 (FERM BP-491) strain was shakingly cultured at 30° C. in medium composed with 3% of glucose, 4% (V/V) of ethanol, 6% (V/V) of acetic acid, 0.5% of yeast extract (manufactured by Daigo Nutrient Chemistry Co., Ltd.) and 0.2% of polypeptone (manufactured by Daigo Nutrient Chemistry Co., Ltd.). After the incubation, the cells were harvested by centrifugation and 4 mg of the ADH complex was then obtained in a conventional manner (the method disclosed in Japanese Patent Application Laid-Open No. 63-12278). This complex was subjected to SDS-polyacrylamide gel electrophoresis to separate the protein having a molecular weight of about 72,000 and the protein having a molecular weight of about 44,000. The respective proteins were eluted from the gel in a conventional manner and provided as samples for the following experiment.

Each 0.1 mg of the samples obtained was subcutaneously injected to rabbit together with complete Freund's adjuvant, and 0.1 mg of each sample was further injected after about 2 weeks. One month after the first injection, rabbit blood was withdrawn from the ear and centrifuged. The reactivity of the thus obtained serum with the two proteins was examined, whereby precipitation was noted. Further after SDS-polyacrylamide gel electrophoresis, its specificity was examined by Western blotting, using the cell-free extract of *Acetobacter altoacetigenes* MH-24 and *E. coli* JM 109. Reactivity with proteins other than the objective protein was not appreciable but the antibody having high specificity was produced.

Cloning of gene containing the full length of the structural gene of ADH complex The Pst I fragment having a size of about 7.0 kilo base containing the structural gene of the protein having a molecular weight of 72,000, which constructed the ADH complex, obtained by the procedures described above and the Sma I fragment having a size of about 4.5 kilo base were ligated at the Pst I site or Sma I site of *E. coli* vector pUC18, respectively, in a conventional manner. The ligated chimera plasmid was transformed to *E. coli* JM 109 in a conventional manner to give transformants carrying the chimera plasmids. From the transformants, the plasmids were prepared in a conventional manner followed by analysis with restriction enzymes.

By the analysis with restriction enzymes, selection was made on the chimera plasmids in which the Pst I fragment or the Sma I fragment was inserted in such a fashion that the transcription direction of lac promoter of *E. coli* vector pUC18 was the same as the transcription direction of the structural gene of the protein having a molecular weight of about 72,000, which constructed the ADH complex. The transformants carrying these plasmids were cultured at 37° C. for 8 hours in LB medium containing 30 μg/ml of ampicillin and 1 mM of isopropyl-β-thiogalactopyranoside (IPTG) to LB medium. The cells were sonicated, and the resulting homogenate was subjected to SDS-polyacrylamide gel electrophoresis. A molecular weight of the protein specifically reacting with the antibody was determined using an antibody capable of specifically reacting with the two proteins which constructed the ADH complex described above, according to the Western blotting method (Annal. Biochem., 112, 195 (1981)). When detection was made using the antibody to the protein having a molecular weight of about 72,000, the reaction with the protein having a molecular weight of about 72,000 was noted both in the case of carrying the Pst I fragment and in the case of carrying the Sma I fragment. In the transformant carrying vector pUC18 alone which was used for control, any protein capable of reacting with the antibody was not detected. From the foregoing, it was confirmed that the structural gene of the protein having a molecular weight of about 72,000 was present on the Pst I fragment and on the Sma I fragment.

On the other hand, detection was made using the antibody to the protein having a molecular weight of about 44,000. In the transformant carrying only vector pUC18 that was used for control, any protein capable of reacting with the antibody was not noted. However, in the transformant carrying the plasmid into which the Sma I fragment had been inserted, the reaction with the protein having a molecular weight of about 24,000 was noted. Further in the transformant carrying the plasmid into which the Pst I fragment had been inserted, the reaction with the protein having a molecular weight of about 44,000 was noted. To the contrary, in the cells cultured in liquid medium containing no IPTG, the protein having a molecular weight of about 44,000 and capable of reacting with the antibody was not detected.

These results indicate that the structural gene encoding the protein having a molecular weight of about 44,000, which is cytochrome c, is present on the Pst I fragment and the direction of its transcription is the same as that of the protein having a molecular weight of about 72,000. From the fact that the molecular weight is about 44,000, it is also assumed that the region of the structural gene necessary for encoding this protein would be about 1.2 kilo base. Taking the size of the protein capable of reacting with the antibody into account, it is assumed that the structural gene of cytochrome c having a molecular weight of about 44,000 would be present immediately downstream the structural gene of the protein having a molecular weight of about 72,000 and transcribed and expressed in one unit.

Based on the foregoing results, it was confirmed that the structural genes of the protein having a molecular weight of about 72,000 and the protein having a molecular weight of about 44,000 are present on the gene fragment cleaved with Pst I in the restriction enzyme map shown in FIG. 1.

Example 2

Transformation of the gene fragment containing the structural gene of ADH complex into acetic acid bacteria host Chimera plasmid pADHS1 of the Sma I fragment (about 4.5 kilo base) containing the structural gene of the protein having a molecular weight of about 72,000, which constructed the ADH complex isolated in EXAMPLE 1 was extracted from *E. coli* ADHS-1 in a conventional manner to give purified DNA. After 1 μg of this DNA was cleaved with Sac I, the cleavage end was rendered blunt with T4 DNA polymerase. On the other hand, plasmid named pTA5001 was prepared from *Acetobacter aceti* No. 1023 [FERM BP-2287 (FERM P-7122)] according to the method described in Agricultural and Biological Chemistry, 49, 1011 (1985) (pTA5001 is described in Agricultural and Biological Chemistry, 49, 1011 (1985). pTA5001 is a mixture of two plasmids of pTA5001A having a molecular weight of 23.5 kilo base and pTA5001B having a molecular weight of 23 kilo base.). After 5 μg of this plasmid DNA was cleaved with Xho I, the cleavage end was rendered blunt with T4 DNA polymerase.

The cleaved DNAs of pADHS1 and pTA5001 prepared as described above were ligated with each other using T4 DNA ligase to give the ligation product. Thereafter, the product was transformed in ADH activity-deleted mutant 10-80 according to the method described in Agricultural and Biological Chemistry, 49, 2091 (1985). The transformants were selected in YPG agar medium (3% of glucose, 0.5% of yeast extract, 0.2% of polypeptide, 2% of agar, pH 6.5) containing 50 μg/ml of ampicillin. Plasmids of 10 ampicillin-resistant strains grown in the selection medium were analyzed by a modified method of Agricultural and Biological Chemistry, 49, 2083 (1985). As the result, the size of the plasmids introduced were all about 31 kilo base. Analysis with restriction enzymes reveals that they were all chimera plasmid of three: pUC18, the Sma I fragment of 4.5 kilo base containing the structural gene of the protein having a molecular weight of about 72,000 which constructed the ADH complex, and pTA5001. This chimera plasmid was named pMADHS1.

After pADHP1 was cleaved with Sac I as in pADHS1, chimera plasmid of plasmid pADH1 isolated in EXAMPLE and pTA5001 was prepared in a manner similar to the case of pADHS1. The chimera plasmid was transformed into mutant 10-80 of *Acetobacter aceti* No. 1023 to give the transformant carrying the chimera plasmid (named pMADHP1).

Properties of acetic acid bacteria transformant

With respect to the two transformants of mutant 10-80 of *Acetobacter aceti* No. 1023 obtained above, enzyme activity of ADH was assayed. Firstly, ampicillin was added to YPG liquid medium (medium having a composition obtained by removing agar from YPG agar medium described above) in a concentration of 30 μg/ml followed by shaking-culture at 30° C. for 36 hours. After culturing, the cells were harvested, suspended in McIlvaine buffer (pH 6.0) and homogenized with a French press. ADH activity in the supernatant obtained from the homogenate was measured by a method of Agricultural and Biological Chemistry, 49, 2045 (1978). At the same time, aldehyde dehydrogenase (ALDH) activity was also determined by a method of Agricultural and Biological Chemistry, 44, 503 (1980). These results are shown in Table 1.

TABLE 1

| Strain | Chimera Plasmid Carried | Enzyme Activity (U/mg protein) | |
|---|---|---|---|
| | | ADH | ALDH |
| No. 1023 | none | 0.28 | 0.94 |
| 10-80 | none | 0.01 | 0.85 |
| 10-80 | pMADHS1 | 0.01 | 0.90 |
| 10-80 | pMADHP1 | 0.40 | 1.00 |

Mutant 10-80 obtained from *Acetobacter aceti* No. 1023 is a strain which is specifically deleted of ADH activity. The transformant of this strain carrying plasmid pMADHS1 containing the structural gene alone encoding the protein having a molecular weight of about 72,000 did not show ADH activity yet. On the other hand, in the transformant carrying plasmid pMADHP1 concurrently containing the gene encoding the protein having a molecular weight of about 44,000, restoration of ADH activity was noted. From the results, it is shown that for expression of ADH activity, two proteins having a molecular weight of 72,00 and a molecular weight of 44,000 which construct the ADH complex are required.

It is also noted that specific activity of the parent having no chimera plasmid was 0.28 (unit/mg protein), whereas the the specific activity of transformant was 0.40, showing an increase of the activity by about 1.4 times.

As described above, the cell content of ADH having the activity can be increased by transforming acetic acid bacteria with the gene containing the structural gene of ADH complex.

Example 3

Determination of nucleotide sequence of the structural gene of the protein having a molecular weight of about 44,000 which constructs the ADH complex The results of EXAMPLE 1 reveal that the structural gene encoding the protein having a molecular weight of about 44,000 is present right at the downstream of the structural gene having a molecular weight of about 72,000. Therefore, regarding about 2.8 kilo base of the fragment containing the region downstream the structural gene having a molecular weight of about 72,000 in the insert fragment of pADHP1, restriction enzyme map of which is shown in FIG. 1 (from the left Cla I site to the right BamH I site in the restriction enzyme map shown in FIG. 1), its nucleotide sequence was determined by the dideoxy method (Methods in Enzymology, 10, 20, Academic Press, New York, 1983), using M13.

Based on the determined nucleotide sequence, the open-reading frame which could encode the protein having a molecular weight of about 44,000 downstream the nucleotide sequence shown in SEQ ID NO. 1 was surveyed and an open-reading frame which could encode the protein of 468 amino acid residues (molecular weight of 49757) composed of 1404 bases starting with translation initiation ATG codon as shown in SEQ ID NO. 2, was found (the amino acid sequence determined from the nucleotide sequence in SEQ ID NO. 2 is shown in SEQ ID No. 4 in FIG. 4). In order to confirm that the polypeptide having the nucleotide sequence shown in SEQ ID NO. 2 coincides with the protein having a molecular weight of about 44,000 which constitutes the membrane-bound alcohol dehydrogenase complex of the present invention, the protein having a molecular weight of about 44,000 was isolated from the membrane-bound alcohol dehydrogenase complex. Lysyl endopeptidase was acted on the protein, the resulting cleavage product was fractionated and the amino terminus amino acid sequence of the resulting peptide was determined, in a manner similar to EXAMPLE 1. It is confirmed that the same amino acid sequence as that determined is present in the sequence shown in SEQ ID NO. 4. That is, lysyl endopeptidase was acted on the protein having a molecular weight of about 44,000 isolated in a manner similar to EXAMPLE 1. The resulting cleavage product was fractionated by HPLC in a manner similar to EXAMPLE 1. Among the eluted peptides, the first and fourth peptides were fractionated in the earlier order of elution. Using about 0.1 mg of the fractionated product, the amino acid sequence at the amino terminus was determined in a manner similar to EXAMPLE 1. As the result, the amino terminal amino acid sequence of the peptide firstly eluted was determined to be Asp-Phe-Tyr-Pro-Ala-Pro and the amino terminal amino acid sequence of the peptide fourthly eluted was determined to be Ser-Leu-Ser-Ala-Glu-Glu.

These sequences coincided with the sequence after 169 and with the sequence after 390, from the amino terminus, in the amino acid sequence shown at the lower column in SEQ ID NO. 4. It was thus confirmed that the gene having the nucleotide sequence shown in FIG. 4 was the structural gene of the protein having a molecular weight of about 44,000 which constituted the ADH complex.

According to the present invention, the structural gene of the ADH complex produced by a series of microorganisms belonging to the genus Acetobacter represented by *Acetobacter altoacetigenes* can be cloned and the structural gene can be successfully incorporated into a plasmid. Further by using acetic acid bacteria transformed by the plasmid, efficiency of acetic acid fermentation can be increased. Moreover, the ADH complex can be readily extracted and purified from the acetic acid bacteria and this enzyme can be utilized for quantitative determination of alcohol.

While the invention has been described in detail and with reference to specific embodiments thereof, it is apparent to one skilled in the art that various changes and modifications can be made therein without departing from the spirit and the scope of the present invention.

What is claimed is:

1. A recombinant plasmid comprising
   (a) vector pUC 18 having an ampicillin resistant gene derived from *E. Coli*,
   (b) a cleaved DNA of pTA 5001 and
   (c) a structural gene of membrane-bound alcohol dehydrogenase complex shown by FIG. 1 and having a molecular size of about 7.0 kilo bases comprising a protein having a molecular weight of about 72,000 as determined by SDS polyacrylamide gel electrophoresis, shown by nucleotide sequence SEQ ID NO. 1 and a protein having a molecular weight of about 44,000 as determined by SDS polyacrylamide gel electrophoresis, shown by nucleotide sequence SEQ ID NO. 2, which are derived from *Acetobacter altoacetigenes*.

2. An acetic acid bacteria belonging to the genus Acetobacter transformed with the recombinant plasmid of claim 1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2214 base pairs
        ( B ) TYPE: nucleic acid
        ( C ) STRANDEDNESS: double
        ( D ) TOPOLOGY: unknown ( i i ) MOLECULE TYPE: genomic DNA ( v i ) ORIGINAL SOURCE:
        ( A ) ORGANISM: Acetobacter altoacetigenes
        ( B ) STRAIN: MH-24

( x ) PUBLICATION INFORMATION:
        ( A ) AUTHORS: Tamaki, Toshimi;
                Fukaya, Masahiro;
                Takemura, Hiroshi;
                Tayama, Kenji;
                Okumura, Hajime;
                Kawamura, Yoshiya;
                Nishiyama, Makoto;
                Horinouchi, Sueharu and
                Beppu, Teruhiko
        ( B ) TITLE: Cloning and Sequencing of the Gene Cluster
                Encoding Two Subunits of Membrane-Bound
                Alcohol Dehydrogenase from Acetobacter
                polyoxogenes
        ( C ) JOURNAL: Biochimica et Biophysica Acta.
        ( D ) VOLUME: 1088
        ( E ) PAGES: 292-300
        ( F ) DATE: 1991

( x i ) SEQUENCE DESCRIPTION: SEQ ID NO:1:

```
ATGATTTCTG  CCGTTTTCGG  AAAAAGACGT  TCTCTGAGCA  GAACGCTTAC  AGCCGGAACG      60

ATATGTGCGG  CTCTCATCTC  CGGGTATGCC  ACCATGGCAT  CCGCAGATGA  CGGGCAGGGC     120

GCCACGGGGG  AAGCGATCAT  CCATGCCGAT  GATCACCCCG  GTAACTGGAT  GACCTATGGC     180

CGCACCTATT  CTGACCAGCG  CTACAGCCCG  CTGGATCAGA  TCAACCGTTC  CAATGTCGGT     240

AACCTGAAGC  TGGCCTGGTA  TCTGGACCTT  GATACCAACC  GTGGCCAGGA  AGGCACGCCC     300

CTGGTTATTG  ATGGCGTCAT  GTACGCCACC  ACCAACTGGA  GCATGATGAA  AGCCGTCGAC     360

GCCGCAACCG  GCAAGCTGCT  GTGGTCCTAT  GACCCGCGCG  TGCCCGGCAA  CATTGCCGAC     420

AAGGGCTGCT  GTGACACGGT  CAACCGTGGC  GCGGCATACT  GGAATGGCAA  GGTCTATTTC     480

GGCACGTTCG  ACGGTCGCCT  GATCGCGCTG  GACGCCAAGA  CCGGCAAGCT  GGTCTGGAGC     540

GTCAACACCA  TTCCGCCCGA  AGCGGAACTG  GGCAAGCAGC  GTTCCTATAC  GGTTGACGGC     600

GCGCCCCGTA  TCGCCAAGGG  CCGCGTGATC  ATCGGTAACG  GTGGTTCCGA  ATTCGGTGCC     660

CGTGGCTTCG  TCAGCGCGTT  CGATGCGGAA  ACCGGCAAGG  TCGACTGGCG  CTTCTTCACG     720

GTTCCGAACC  CCAAGAACGA  ACCGGACGCT  GCATCCGACA  GCGTGCTGAT  GAACAAGGCC     780

TACCAGACCT  GGAGCCCGAC  CGGCGCCTGG  ACCCGCCAGG  GTGGCGGCGG  CACGGTATGG     840
```

| | | | | | | |
|---|---|---|---|---|---|---|
|GATTCCATCG|TGTATGACCC|CGTGGCCGAC|CTGGTCTACC|TGGGCGTTGG|CAACGGTTCG|900|
|CCGTGGAACT|ACAAGTACCG|TTCCGAAGGC|AAGGGCGACA|ACCTGTTCCT|GGGCAGCATC|960|
|GTCGCACTGA|AGCCGGAAAC|CGGCGAATAC|GTCTGGCATT|TCCAGGAAAC|GCCGATGGAC|1020|
|CAGTGGGACT|TCACCTCGGA|CCAGCAGATC|ATGACGCTTG|ACCTGCCGAT|CAATGGTGAA|1080|
|ACCCGCCACG|TCATCGTCCA|TGCGCGCAAG|AACGGCTTCT|TCTACATCAT|CGATGCGAAG|1140|
|ACCGGTGAGT|TCATCTCGGG|CAAGAACTAC|GTCTATGTGA|ACTGGGCCAG|CGGCCTTGAT|1200|
|CCCAAGACCG|GCCGTCCGAT|CTACAACCCC|GATGCGCTCT|ACACCCTTAC|GGGCAAGGAA|1260|
|TGGTACGGCA|TTCCGGGTGA|CCTTGGCGGC|CATAACTTCG|CGGCCATGGC|GTTCAGCCCC|1320|
|AAGACCGGGC|TGGTCTATAT|TCCGGCGCAG|CAGGTTCCGT|TCCTGTACAC|CAATCAGGTC|1380|
|GGTGGCTTCA|CGCCGCACCC|CGACAGCTGG|AACCTGGGTC|TGGACATGAA|CAAGGTCGGT|1440|
|ATTCCCGACT|CGCCTGAAGC|CAAGCAGGCC|TTCGTGAAGG|ACCTGAAGGG|CTGGATCGTG|1500|
|GCCTGGGATC|CGCAGAAGCA|GGCTGAAGCA|TGGCGCGTGG|ACCACAAGGG|GCCGTGGAAC|1560|
|GGCGGTATCC|TGGCAACTGG|CGGCGACCTG|CTGTTCCAGG|GCTTGGCGAA|CGGCGAATTC|1620|
|CATGCCTATG|ACGCGACGAA|CGGTTCCGAC|CTGTTCCACT|TCGCGGCGGA|CAGCGGCATC|1680|
|ATCGCACCGC|CTGTGACCTA|CCTTGCCAAT|GGCAAGCAGT|ATGTTGCGGT|TGAAGTGGGC|1740|
|TGGGGCGGCA|TCTATCCGTT|CTTCCTTGGT|GGCCTGGCCC|GTACCAGCGG|CTGGACCGTC|1800|
|AACCACTCGC|GCATCATTGC|CTTCTCGCTC|GATGGCAAGT|CCGGCCCGCT|GCCCAAGCAG|1860|
|AATGACCAGG|GCTTCCTGCC|CGTCAAGCCG|CCGGCACAGT|TCGACAGCAA|GCGTACCGAT|1920|
|AACGGTTACT|TCCAGTTCCA|GACCTATTGC|GCCGCCTGTC|ATGGCGATAA|CGCAGAAGGT|1980|
|GCCGGTGTGC|TGCCTGACCT|GCGCTGGTCC|GGGTCCATCC|GTCATGAGGA|CGCGTTCTAC|2040|
|AATGTTGTCG|GCCGCGGCGC|GCTTACCGCC|TACGGTATGG|ATCGCTTGCA|CGGTAACATG|2100|
|AACCCGACCG|AGATTGAGGA|CATCCGCCAG|TTCCTGATCA|AGCGTGCGAA|CGAGACCTAT|2160|
|CAGAGGGAAG|TTGATGCCCG|GAAGAACGCT|GACGGTATCC|CCGAGCAGCT|GCCG|2214|

( 2 ) INFORMATION FOR SEQ ID NO:2:

( i ) SEQUENCE CHARACTERISTICS:
        ( A ) LENGTH: 1404 base pairs
        ( B ) TYPE: nucleic acid
        ( C ) STRANDEDNESS: double
        ( D ) TOPOLOGY: unknown ( i i ) MOLECULE TYPE: genomic DNA ( v i ) ORIGINAL SOURCE:
        ( A ) ORGANISM: Acetobacter altoacetigenes
        ( B ) STRAIN: MH-24

( x ) PUBLICATION INFORMATION:
        ( A ) AUTHORS: Tamaki, Toshimi;
            Fukaya, Masahiro;
            Takemura, Hiroshi;
            Tayama, Kenji;
            Okumura, Hajime;
            Kawamura, Yoshiya;
            Nishiyama, Makoto;
            Horinouchi, Sueharu and
            Beppu, Teruhiko
        ( B ) TITLE: Cloning and Sequencing of the Gene Cluster
            Encoding Two Subunits of Membrane-Bound
            Alcohol Dehydrogenase from Acetobacter
            polyoxogenes
        ( C ) JOURNAL: Biochimica et Biophysica Acta.
        ( D ) VOLUME: 1088
        ( E ) PAGES: 292-300
        ( F ) DATE: 1991

( x i ) SEQUENCE DESCRIPTION: SEQ ID NO:2:

```
ATGATCAACA GACTTAAGGT GACATTCAGC GCGGCAGCGT TTAGTCTGCT GGCAGGGACG    60
GCATTGGCAC AGACGCCAGA TGCTGACTCC GCGCTGGTCC AGAAGGGGGC ATATGTCGCG   120
CGACTGGGTG ACTGCGTAGC ATGTCATACC GCTCTCCATG GACAGTCGTA CGCAGGCGGG   180
CTTGAAATCA AGAGCCCGAT CGGTACGATC TACTCCACGA ACATCACACC GGACCCGACC   240
TACGGTATCG GTCGCTACAC CTTCGCCGAA TTCGACGAAG CCGTGCGCCA TGGTATCCGC   300
AAGGACGGTT CCACGCTGTA TCCGGCCATG CCGTATCCCT CCTTCTCGCG CATGACGAAG   360
GAAGACATGC AGGCGCTGTA TGCGTACTTC ATGCATGGGG TGAAGCCGGT CGCGCAGCCG   420
GACAAGCAGC CGGACATCTC CTGGCCCTTG TCCATGCGCT GGCCGCTGGG CATCTGGCGC   480
ATGATGTTCT CGCCTTCGCC GAAGGACTTC ACGCCGGCGC CAGGCACGGA TCCTGAAATC   540
GCACGTGGCG ATTATCTGGT TACCGGCCCC GGGCATTGCG GTGCGTGTCA TACCCCGCGT   600
GGCTTCGCCA TGCAGGAAAA GGCGCTGGAC GCTGCCGGTG GTCCTGACTT CCTGTCCGGT   660
GGCGCACCGA TCGACAACTG GGTCGCGCCG AGCCTGCGCA ACGATCCTGT CGTTGGTCTG   720
GGCCGCTGGT CCGAGGATGA CATCTACACC TTCCTGAAGT CCGGCCGTAT CGACCACTCC   780
GCCGTGTTCG GTGGCATGGG CGATGTGGTG GCATGGAGCA CCCAGTACTT CACCGATGAC   840
GACCTGCACG CCATCGCGAA GTACCTGAAG AGCCTGCCGC CGGTGCCGCC GTCACAGGGC   900
AACTACACCT ACGATCCGTC CACCGCGAAC ATGCTGGCTT CGGGTAATAC CGCCAGCGTT   960
CCGGGTGCTG ATACGTATGT GAAGGAATGC GCCATCTGTC ACCGTAACGA CGGTGGTGGC  1020
GTGGCCCGCA TGTTCCCGCC GCTGGCTGGC AACCCGGTTG TCGTGACCGA GAACCCGACC  1080
TCGCTGGTGA ACGTGATTGC GCATGGTGGC GTGCTGCCGC CGAGCAACTG GGCACCGTCC  1140
GCAGTGGCAA TGCCGGGTTA CAGCAAGTCG CTGTCCGCCC AGCAGATTGC TGATGTGGTC  1200
AACTTCATCC GCACCAGCTG GGGCAACAAG GCGCCCGGCA CCGTTACGGC TGCGGATGTT  1260
ACCAAGCTGC GCGACACGGG CGCCCCGGTT TCCAGCTCTG GCTGGAACAG CGTGAGCAGC  1320
GGCTGGTCGG TCTTCCTGCC GCAGCCTTAC GGCTCGGGCT GGACGTTTGC CCCGCAGACG  1380
CACACCGGTC AGGACGCCGC ACAG                                         1404
```

( 2 ) INFORMATION FOR SEQ ID NO:3:

( i ) SEQUENCE CHARACTERISTICS:
    ( A ) LENGTH: 738 amino acids
    ( B ) TYPE: amino acid
    ( C ) TOPOLOGY: unknown ( i i ) MOLECULE TYPE: protein ( i x ) FEATURE:
    ( A ) NAME/KEY: MATURE PEPTIDE
    ( B ) LOCATION: 36 to 738
    ( C ) IDENTIFICATION METHOD: N- terminal sequences of the
      purified protein having a molecular weight of about
      72,000

( v i ) ORIGINAL SOURCE:
    ( A ) ORGANISM: Acetobacter altoacetigenes
    ( B ) STRAIN: MH-24

( x ) PUBLICATION INFORMATION:
    ( A ) AUTHORS: Tamaki, Toshimi;
      Fukaya, Masahiro;
      Takemura, Hiroshi;
      Tayama, Kenji;
      Okumura, Hajime;
      Kawamura, Yoshiya;
      Nishiyama, Makoto;
      Horinouchi, Sueharu and
      Beppu, Teruhiko
    ( B ) TITLE: Cloning and Sequencing of the Gene Cluster
      Encoding Two Subunits of Membrane-Bound Alcohol Dehydrogenase from Acetobacter polyoxogenes
(C) JOURNAL: Biochimica et Biophysica Acta.
(D) VOLUME: 1088
(E) PAGES: 292-300
(F) DATE: 1991

(xi) SEQUENCE DESCRIPTION: SEQ ID NO:3:

```
Met Ile Ser Ala Val Phe Gly Lys Arg Arg Ser Leu Ser Arg Thr Leu
 1               5                  10                  15

Thr Ala Gly Thr Ile Cys Ala Ala Leu Ile Ser Gly Tyr Ala Thr Met
            20                  25                  30

Ala Ser Ala Asp Asp Gly Gln Gly Ala Thr Gly Glu Ala Ile Ile His
        35                  40                  45

Ala Asp Asp His Pro Gly Asn Trp Met Thr Tyr Gly Arg Thr Tyr Ser
    50                  55                  60

Asp Gln Arg Tyr Ser Pro Leu Asp Gln Ile Asn Arg Ser Asn Val Gly
65                  70                  75                  80

Asn Leu Lys Leu Ala Trp Tyr Leu Asp Leu Asp Thr Asn Arg Gly Gln
            85                  90                  95

Glu Gly Thr Pro Leu Val Ile Asp Gly Val Met Tyr Ala Thr Thr Asn
            100                 105                 110

Trp Ser Met Met Lys Ala Val Asp Ala Ala Thr Gly Lys Leu Leu Trp
            115                 120                 125

Ser Tyr Asp Pro Arg Val Pro Gly Asn Ile Ala Asp Lys Gly Cys Cys
    130                 135                 140

Asp Thr Val Asn Arg Gly Ala Ala Tyr Trp Asn Gly Lys Val Tyr Phe
145                 150                 155                 160

Gly Thr Phe Asp Gly Arg Leu Ile Ala Leu Asp Ala Lys Thr Gly Lys
            165                 170                 175

Leu Val Trp Ser Val Asn Thr Ile Pro Pro Glu Ala Glu Leu Gly Lys
            180                 185                 190

Gln Arg Ser Tyr Thr Val Asp Gly Ala Pro Arg Ile Ala Lys Gly Arg
        195                 200                 205

Val Ile Ile Gly Asn Gly Gly Ser Glu Phe Gly Ala Arg Gly Phe Val
    210                 215                 220

Ser Ala Phe Asp Ala Glu Thr Gly Lys Val Asp Trp Arg Phe Phe Thr
225                 230                 235                 240

Val Pro Asn Pro Lys Asn Glu Pro Asp Ala Ala Ser Asp Ser Val Leu
                245                 250                 255

Met Asn Lys Ala Tyr Gln Thr Trp Ser Pro Thr Gly Ala Trp Thr Arg
            260                 265                 270

Gln Gly Gly Gly Gly Thr Val Trp Asp Ser Ile Val Tyr Asp Pro Val
        275                 280                 285

Ala Asp Leu Val Tyr Leu Gly Val Gly Asn Gly Ser Pro Trp Asn Tyr
    290                 295                 300

Lys Tyr Arg Ser Glu Gly Lys Gly Asp Asn Leu Phe Leu Gly Ser Ile
305                 310                 315                 320

Val Ala Leu Lys Pro Glu Thr Gly Glu Tyr Val Trp His Phe Gln Glu
            325                 330                 335

Thr Pro Met Asp Gln Trp Asp Phe Thr Ser Asp Gln Gln Ile Met Thr
            340                 345                 350

Leu Asp Leu Pro Ile Asn Gly Glu Thr Arg His Val Ile Val His Ala
        355                 360                 365

Arg Lys Asn Gly Phe Phe Tyr Ile Ile Asp Ala Lys Thr Gly Glu Phe
    370                 375                 380

Ile Ser Gly Lys Asn Tyr Val Tyr Val Asn Trp Ala Ser Gly Leu Asp
```

|   | 385 |   |   |   | 390 |   |   |   | 395 |   |   |   | 400 |
|---|---|---|---|---|---|---|---|---|---|---|---|---|---|

Pro Lys Thr Gly Arg Pro Ile Tyr Asn Pro Asp Ala Leu Tyr Thr Leu
         405             410             415

Thr Gly Lys Glu Trp Tyr Gly Ile Pro Gly Asp Leu Gly Gly His Asn
         420             425             430

Phe Ala Ala Met Ala Phe Ser Pro Lys Thr Gly Leu Val Tyr Ile Pro
         435             440             445

Ala Gln Gln Val Pro Phe Leu Tyr Thr Asn Gln Val Gly Gly Phe Thr
450                 455             460

Pro His Pro Asp Ser Trp Asn Leu Gly Leu Asp Met Asn Lys Val Gly
465             470             475             480

Ile Pro Asp Ser Pro Glu Ala Lys Gln Ala Phe Val Lys Asp Leu Lys
             485             490             495

Gly Trp Ile Val Ala Trp Asp Pro Gln Lys Gln Ala Glu Ala Trp Arg
         500             505             510

Val Asp His Lys Gly Pro Trp Asn Gly Gly Ile Leu Ala Thr Gly Gly
         515             520             525

Asp Leu Leu Phe Gln Gly Leu Ala Asn Gly Glu Phe His Ala Tyr Asp
     530             535             540

Ala Thr Asn Gly Ser Asp Leu Phe His Phe Ala Ala Asp Ser Gly Ile
545             550             555             560

Ile Ala Pro Pro Val Thr Tyr Leu Ala Asn Gly Lys Gln Tyr Val Ala
             565             570             575

Val Glu Val Gly Trp Gly Gly Ile Tyr Pro Phe Phe Leu Gly Gly Leu
         580             585             590

Ala Arg Thr Ser Gly Trp Thr Val Asn His Ser Arg Ile Ile Ala Phe
         595             600             605

Ser Leu Asp Gly Lys Ser Gly Pro Leu Pro Lys Gln Asn Asp Gln Gly
     610             615             620

Phe Leu Pro Val Lys Pro Pro Ala Gln Phe Asp Ser Lys Arg Thr Asp
625             630             635             640

Asn Gly Tyr Phe Gln Phe Gln Thr Tyr Cys Ala Ala Cys His Gly Asp
             645             650             655

Asn Ala Glu Gly Ala Gly Val Leu Pro Asp Leu Arg Trp Ser Gly Ser
         660             665             670

Ile Arg His Glu Asp Ala Phe Tyr Asn Val Val Gly Arg Gly Ala Leu
     675             680             685

Thr Ala Tyr Gly Met Asp Arg Leu His Gly Asn Met Asn Pro Thr Glu
690             695             700

Ile Glu Asp Ile Arg Gln Phe Leu Ile Lys Arg Ala Asn Glu Thr Tyr
705             710             715             720

Gln Arg Glu Val Asp Ala Arg Lys Asn Ala Asp Gly Ile Pro Glu Gln
             725             730             735

Leu Pro
    738

( 2 ) INFORMATION FOR SEQ ID NO:4:

( i ) SEQUENCE CHARACTERISTICS:
        ( A ) LENGTH: 468 amino acids
        ( B ) TYPE: amino acid
        ( D ) TOPOLOGY: unknown ( i i ) MOLECULE TYPE: protein ( i x ) FEATURE:
        ( A ) NAME/KEY: MATURE PEPTIDE
        ( B ) LOCATION: 24 to 468
        ( C ) IDENTIFICATION METHOD: similarity of other signal sequences (vi) ORIGINAL SOURCE:
  (A) ORGANISM: Acetobacter altoacetigenes
  (B) STRAIN: MH-24

(x) PUBLICATION INFORMATION:
  (A) AUTHORS: Tamaki, Toshimi;
    Fukaya, Masahiro;
    Takemura, Hiroshi;
    Tayama, Kenji;
    Okumura, Hajime;
    Kawamura, Yoshiya;
    Nishiyama, Makoto;
    Horinouchi, Sueharu and
    Beppu, Teruhiko
  (B) TITLE: Cloning and Sequencing of the Gene Cluster
    Encoding Two Subunits of Membrane-Bound
    Alcohol Dehydrogenase from Acetobacter
    polyoxogenes
  (C) JOURNAL: Biochimica et Biophysica Acta.
  (D) VOLUME: 1088
  (E) PAGES: 292-300
  (F) DATE: 1991

(xi) SEQUENCE DESCRIPTION: SEQ ID NO:4:

| Met | Ile | Asn | Arg | Leu | Lys | Val | Thr | Phe | Ser | Ala | Ala | Ala | Phe | Ser | Leu |
|---|---|---|---|---|---|---|---|---|---|---|---|---|---|---|---|
| 1 | | | | 5 | | | | | 10 | | | | | 15 | |

| Leu | Ala | Gly | Thr | Ala | Leu | Ala | Gln | Thr | Pro | Asp | Ala | Asp | Ser | Ala | Leu |
|---|---|---|---|---|---|---|---|---|---|---|---|---|---|---|---|
| | | | 20 | | | | | 25 | | | | | 30 | | |

| Val | Gln | Lys | Gly | Ala | Tyr | Val | Ala | Arg | Leu | Gly | Asp | Cys | Val | Ala | Cys |
|---|---|---|---|---|---|---|---|---|---|---|---|---|---|---|---|
| | | 35 | | | | | 40 | | | | | 45 | | | |

| His | Thr | Ala | Leu | His | Gly | Gln | Ser | Tyr | Ala | Gly | Gly | Leu | Glu | Ile | Lys |
|---|---|---|---|---|---|---|---|---|---|---|---|---|---|---|---|
| | 50 | | | | | 55 | | | | | 60 | | | | |

| Ser | Pro | Ile | Gly | Thr | Ile | Tyr | Ser | Thr | Asn | Ile | Thr | Pro | Asp | Pro | Thr |
|---|---|---|---|---|---|---|---|---|---|---|---|---|---|---|---|
| 65 | | | | | 70 | | | | | 75 | | | | | 80 |

| Tyr | Gly | Ile | Gly | Arg | Tyr | Thr | Phe | Ala | Glu | Phe | Asp | Glu | Ala | Val | Arg |
|---|---|---|---|---|---|---|---|---|---|---|---|---|---|---|---|
| | | | | 85 | | | | | 90 | | | | | 95 | |

| His | Gly | Ile | Arg | Lys | Asp | Gly | Ser | Thr | Leu | Tyr | Pro | Ala | Met | Pro | Tyr |
|---|---|---|---|---|---|---|---|---|---|---|---|---|---|---|---|
| | | | 100 | | | | | 105 | | | | | 110 | | |

| Pro | Ser | Phe | Ser | Arg | Met | Thr | Lys | Glu | Asp | Met | Gln | Ala | Leu | Tyr | Ala |
|---|---|---|---|---|---|---|---|---|---|---|---|---|---|---|---|
| | | 115 | | | | | 120 | | | | | 125 | | | |

| Tyr | Phe | Met | His | Gly | Val | Lys | Pro | Val | Ala | Gln | Pro | Asp | Lys | Gln | Pro |
|---|---|---|---|---|---|---|---|---|---|---|---|---|---|---|---|
| | 130 | | | | | 135 | | | | | 140 | | | | |

| Asp | Ile | Ser | Trp | Pro | Leu | Ser | Met | Arg | Trp | Pro | Leu | Gly | Ile | Trp | Arg |
|---|---|---|---|---|---|---|---|---|---|---|---|---|---|---|---|
| 145 | | | | | 150 | | | | | 155 | | | | | 160 |

| Met | Met | Phe | Ser | Pro | Ser | Pro | Lys | Asp | Phe | Thr | Pro | Ala | Pro | Gly | Thr |
|---|---|---|---|---|---|---|---|---|---|---|---|---|---|---|---|
| | | | | 165 | | | | | 170 | | | | | 175 | |

| Asp | Pro | Glu | Ile | Ala | Arg | Gly | Asp | Tyr | Leu | Val | Thr | Gly | Pro | Gly | His |
|---|---|---|---|---|---|---|---|---|---|---|---|---|---|---|---|
| | | | 180 | | | | | 185 | | | | | 190 | | |

| Cys | Gly | Ala | Cys | His | Thr | Pro | Arg | Gly | Phe | Ala | Met | Gln | Glu | Lys | Ala |
|---|---|---|---|---|---|---|---|---|---|---|---|---|---|---|---|
| | | 195 | | | | | 200 | | | | | 205 | | | |

| Leu | Asp | Ala | Ala | Gly | Gly | Pro | Asp | Phe | Leu | Ser | Gly | Gly | Ala | Pro | Ile |
|---|---|---|---|---|---|---|---|---|---|---|---|---|---|---|---|
| | 210 | | | | | 215 | | | | | 220 | | | | |

| Asp | Asn | Trp | Val | Ala | Pro | Ser | Leu | Arg | Asn | Asp | Pro | Val | Val | Gly | Leu |
|---|---|---|---|---|---|---|---|---|---|---|---|---|---|---|---|
| 225 | | | | | 230 | | | | | 235 | | | | | 240 |

| Gly | Arg | Trp | Ser | Glu | Asp | Asp | Ile | Tyr | Thr | Phe | Leu | Lys | Ser | Gly | Arg |
|---|---|---|---|---|---|---|---|---|---|---|---|---|---|---|---|
| | | | | 245 | | | | | 250 | | | | | 255 | |

| Ile | Asp | His | Ser | Ala | Val | Phe | Gly | Gly | Met | Gly | Asp | Val | Val | Ala | Trp |
|---|---|---|---|---|---|---|---|---|---|---|---|---|---|---|---|
| | | | 260 | | | | | 265 | | | | | 270 | | |

| Ser | Thr | Gln | Tyr | Phe | Thr | Asp | Asp | Asp | Leu | His | Ala | Ile | Ala | Lys | Tyr |
|---|---|---|---|---|---|---|---|---|---|---|---|---|---|---|---|
| | | 275 | | | | | 280 | | | | | 285 | | | |

| Leu | Lys | Ser | Leu | Pro | Pro | Val | Pro | Pro | Ser | Gln | Gly | Asn | Tyr | Thr | Tyr |

|     | 290 |     |     |     | 295 |     |     |     | 300 |     |     |     |     |
| --- | --- | --- | --- | --- | --- | --- | --- | --- | --- | --- | --- | --- | --- |
| Asp 305 | Pro | Ser | Thr | Ala | Asn 310 | Met | Leu | Ala | Ser | Gly 315 | Asn | Thr | Ala | Ser | Val 320 |
| Pro | Gly | Ala | Asp | Thr 325 | Tyr | Val | Lys | Glu | Cys 330 | Ala | Ile | Cys | His | Arg 335 | Asn |
| Asp | Gly | Gly | Gly 340 | Val | Ala | Arg | Met | Phe 345 | Pro | Pro | Leu | Ala | Gly 350 | Asn | Pro |
| Val | Val | Val 355 | Thr | Glu | Asn | Pro | Thr 360 | Ser | Leu | Val | Asn | Val 365 | Ile | Ala | His |
| Gly | Gly 370 | Val | Leu | Pro | Pro | Ser 375 | Asn | Trp | Ala | Pro | Ser 380 | Ala | Val | Ala | Met |
| Pro 385 | Gly | Tyr | Ser | Lys | Ser 390 | Leu | Ser | Ala | Gln | Gln 395 | Ile | Ala | Asp | Val | Val 400 |
| Asn | Phe | Ile | Arg | Thr 405 | Ser | Trp | Gly | Asn | Lys 410 | Ala | Pro | Gly | Thr | Val 415 | Thr |
| Ala | Ala | Asp | Val 420 | Thr | Lys | Leu | Arg | Asp 425 | Thr | Gly | Ala | Pro | Val 430 | Ser | Ser |
| Ser | Gly | Trp 435 | Asn | Ser | Val | Ser | Ser 440 | Gly | Trp | Ser | Val | Phe 445 | Leu | Pro | Gln |
| Pro | Tyr 450 | Gly | Ser | Gly | Trp | Thr 455 | Phe | Ala | Pro | Gln | Thr 460 | His | Thr | Gly | Gln |
| Asp 465 | Ala | Ala | Gln 468 |